(12) United States Patent
Stolka et al.

(10) Patent No.: US 9,844,360 B2
(45) Date of Patent: Dec. 19, 2017

(54) SYSTEM AND DEVICES FOR IMAGE TARGETING

(71) Applicant: Clear Guide Medical, LLC, Baltimore, MD (US)

(72) Inventors: Philipp Jakob Stolka, Baltimore, MD (US); Pezhman Foroughi, Cockeysville, MD (US); Matthew C. Rendina, Baltimore, MD (US); Gregory Donald Hager, Baltimore, MD (US)

(73) Assignee: CLEAR GUIDE MEDICAL, INC., Baltimore, MD (US)

( * ) Notice: Subject to any disclaimer, the term of this patent is extended or adjusted under 35 U.S.C. 154(b) by 436 days.

(21) Appl. No.: 14/524,468

(22) Filed: Oct. 27, 2014

(65) Prior Publication Data

US 2016/0113724 A1     Apr. 28, 2016

(51) Int. Cl.
*A61B 8/00*       (2006.01)
*A61B 8/08*       (2006.01)
(Continued)

(52) U.S. Cl.
CPC .......... *A61B 8/4444* (2013.01); *A61B 5/0077* (2013.01); *A61B 5/066* (2013.01); *A61B 8/0841* (2013.01); *A61B 8/4254* (2013.01); *A61B 8/46* (2013.01); *A61B 8/466* (2013.01); *A61B 8/52* (2013.01); *A61B 8/54* (2013.01); *A61B 34/20* (2016.02); *A61B 34/76* (2016.02); *G06F 3/016* (2013.01); *A61B 5/055* (2013.01); *A61B 5/743* (2013.01); *A61B 8/464* (2013.01); *A61B 2017/3413* (2013.01); *A61B 2034/2057* (2016.02); *A61B 2034/2063* (2016.02); (Continued)

(58) Field of Classification Search
None
See application file for complete search history.

(56) References Cited

U.S. PATENT DOCUMENTS 5,834,759 A * 11/1998 Glossop ................. G01S 5/163
                                                           250/203.1
6,014,473 A    1/2000 Hossack et al.
(Continued)

OTHER PUBLICATIONS

Goldsmith, A. M., P. C. Pedersen, and T. L. Szabo. "An inertial-optical tracking system for portable, quantitative, 3D ultrasound." Ultrasonics Symposium, 2008. IUS 2008. IEEE. IEEE, 2008.*

(Continued)

*Primary Examiner* — Christopher Cook
*Assistant Examiner* — Carolyn Pehlke
(74) *Attorney, Agent, or Firm* — Venable LLP; Henry J. Daley

(57) ABSTRACT

A medical imaging system may include an imaging device; an optical head coupled to the imaging device, the optical head comprising a plurality of optical sensors; and a control unit in communication with the optical head. The control unit may be configured to: receive data from the plurality of optical sensors, determine a subset of optical sensors from the plurality of optical sensors for viewing one or more visible targets based on the received data from the plurality of optical sensors, and instruct the optical head to transmit images from the subset of optical sensors.

22 Claims, 11 Drawing Sheets

(51) Int. Cl.
  *A61B 34/00*  (2016.01)
  *A61B 5/00*   (2006.01)
  *G06F 3/01*   (2006.01)
  *A61B 5/06*   (2006.01)
  *A61B 34/20*  (2016.01)
  *A61B 5/055*  (2006.01)
  *A61B 17/34*  (2006.01)

(52) U.S. Cl.
  CPC ............... *A61B 2560/0238* (2013.01); *A61B 2562/0233* (2013.01)

(56) References Cited

U.S. PATENT DOCUMENTS

| | | |
|---|---|---|
| 2002/0062077 A1 | 5/2002 | Emmenegger et al. |
| 2008/0300817 A1 | 12/2008 | Bieswanger et al. |
| 2012/0249802 A1 | 10/2012 | Taylor |
| 2013/0016185 A1 | 1/2013 | Stolka et al. |
| 2013/0245428 A1 | 9/2013 | Banjanin et al. |
| 2014/0171799 A1* | 6/2014 | Hershey ............... A61B 8/4254 600/440 |

OTHER PUBLICATIONS

Stolka, Philipp J., et al. "Needle guidance using handheld stereo vision and projection for ultrasound-based interventions." International Conference on Medical Image Computing and Computer-Assisted Intervention. Springer International Publishing, Sep. 18, 2014.*

Wingrave, Chadwick A., et al. "The wiimote and beyond: Spatially convenient devices for 3d user interfaces." IEEE Computer Graphics and Applications 30.2 (2010): 71-85.*

Stolka et al., "Navigation with local sensors in handheld 3d ultrasound: initial in-vivo experience," SPIE Medical Imaging 2011, pp. 79681J-79681J.

Wang et al., "The Kinect as an Interventional Tracking System," SPIE Medical Imaging, 2012, pp. 93160U-83160U.

Zhang et al., "A flexible new technique for camera calibration," 2000, IEEE Transactions on Pattern Analysis and Machine Intelligence.

International Search Report and Written Opinion issued in PCT Application No. PCT/US2015/057519 dated Mar. 4, 2016.

* cited by examiner

US 9,844,360 B2

SYSTEM AND DEVICES FOR IMAGE TARGETING

BACKGROUND

1. Field of Invention

The field of the currently claimed embodiments of this invention relate to image guidance, and more particularly to imaging devices with a plurality of sensors for observation and tracking of the environment or one or more tools.

2. Discussion of Related Art

In image-guided interventions, the tracking and localization of imaging devices and medical tools during procedures are considered the main enabling technology in image-guided surgery (IGS) systems.

Limitations of the current approach on both the research and commercial sides may be attributed to the available tracking technologies and to the feasibility of integrating these systems and using them in clinical environments. Thus, there remains a need for improved imaging devices for use in image-guided surgery.

SUMMARY

Aspects of the invention may involve systems and devices. In one embodiment, a system for medical imaging may be provided. The system may include an imaging device; an optical head coupled to the imaging device, the optical head comprising a plurality of optical sensors; and a control unit in communication with the optical head. The control unit may be configured to: receive data from the plurality of optical sensors, determine a subset of optical sensors from the plurality of optical sensors for viewing one or more visible targets (e.g., one or more instruments, an environment, a patient, or a handheld device) based on the received data from the plurality of optical sensors, and instruct the optical head to transmit images from the subset of optical sensors.

In another embodiment, an optical tracking device may be provided. The device including a housing configured to be attachable to an ultrasound probe; a printed circuit board (PCB) housed in the housing; and a plurality of optical sensors coupled to the PCB, the plurality of optical sensors spaced evenly apart, the plurality of optical sensors transmitting a plurality of images to a control unit, the plurality of optical sensors configured to receive instructions from the control unit, the instructions including adjusting imaging bandwidth for the plurality of optical sensors.

In another embodiment, an imaging device may be provided. The imaging device including an imaging probe comprising one or more imaging sensors and a handle; an optical head assembly configured to be attachable and detachable to the handle of the imaging probe, wherein the optical head assembly wraps around the handle of the imaging probe and the handle of the imaging probe is configured to accept a physical coupling with the optical head assembly; and a plurality of optical sensors coupled to the optical head assembly.

BRIEF DESCRIPTION OF THE DRAWINGS

Further objectives and advantages will become apparent from a consideration of the description, drawings, and examples.

DETAILED DESCRIPTION

Figure 1:
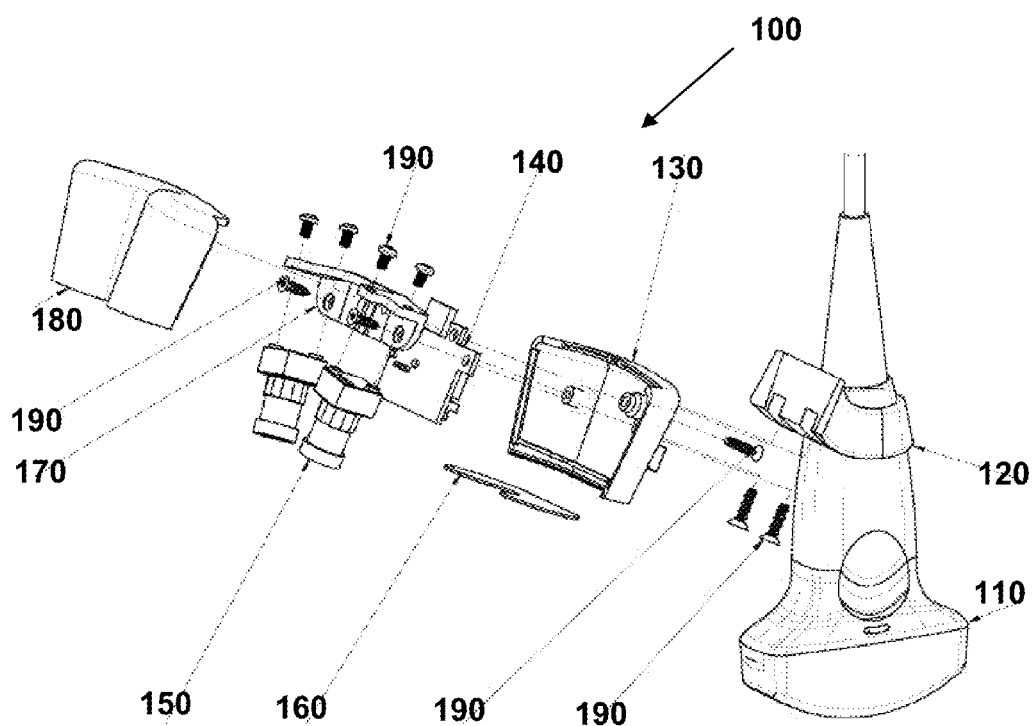
FIG. 1 shows an example imaging component for an imaging system.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of this invention describe IGI-(image-guided interventions)-enabling "platform technology" going beyond the current paradigm of relatively narrow image-guidance and tracking. It simultaneously aims to overcome limitations of tracking, visualization, and guidance; specifically using and integrating techniques e.g. related to needle identification and tracking using 3D computer vision and structured light; and imaging device tracking using local sensing approaches; among others. Examples of IGI may be seen in U.S. patent application Ser. No. 13/511,101, titled "Low-cost image-guided navigation and intervention systems using cooperative sets of local sensors," published as U.S. Patent Application Publication No. 2013/0016185. Furthermore U.S. patent application Ser. Nos. 14/092,843 and 14/092,755 depict sample IGIs. The contents of U.S. patent application Ser. Nos. 13/511,101, 14/092,843, and 14/092,755 are incorporated herein by reference in their entirety.

The current invention covers a wide range of different embodiments, sharing a tightly integrated common core of components and methods used for general imaging, projection, vision, targeting, and local sensing.

Some embodiments of the current invention are directed to combining a group of complementary technologies to provide a local sensing approach that can provide enabling technology for the tracking of targets and guidance of medical devices or tools, for example, with the potential to significantly reduce errors and increase positive patient outcomes. This approach can provide a platform technology for the tracking (e.g., ultrasound probes, the patient, the environment, and/or other imaging devices), intervention guidance, and/or information visualization according to some embodiments of the current invention. By combining ultrasound imaging with image analysis algorithms and probe-mounted light-sensitive devices, feedback devices, independent optical-inertial sensors, according to some embodiments of the current invention, it is possible to reconstruct the position and trajectory of surgical needles and other tools or objects by incrementally tracking and guiding their current motion.

Some embodiments of the current invention allow the segmentation, tracking, and guidance of needles, imaging devices (e.g., ultrasound probes) and other tools, using visual, ultrasound, and/or other imaging and localization modalities and haptic, audio and/or visual feedback.

Such devices can allow imaging procedures with improved sensitivity and specificity as compared to the current state of the art. This can open up several possible application scenarios that previously required harmful X-ray/CT or expensive MRI imaging, and/or external tracking, and/or expensive, imprecise, time-consuming, or impractical hardware setups, or that were simply afflicted with an inherent lack of precision and guarantee of success, such as: biopsies, RF/HIFU ablations etc.: can allow 2D- or 3D-ultrasound-based needle guidance, brachytherapy: can allow 3D-ultrasound acquisition and needle guidance for precise brachytherapy seed placement, other applications relying on tracked imaging and tracked tools.

Some embodiments of the current invention may provide several advantages over existing technologies, such as combinations of: low-cost tracking, local, compact, and non-intrusive solution—ideal tracking system for hand-held and compact ultrasound systems that are primarily used in intervention and point-of-care clinical suites, but also for general needle/tool tracking under visual tracking in other interventional settings.

For example, some embodiments of the current invention are directed to devices and methods for the tracking of imaging devices (e.g., ultrasound probes), the patient, medical tools, and/or the environment. By combining ultrasound imaging with image analysis algorithms and probe-mounted light-sensitive devices it is possible to reconstruct the position and trajectory of tools (e.g., needles, pointers, biopsy tools, laparoscopes, ablation devices, surgical instruments, or elongated tools) and other objects by incrementally tracking their current motion according to an embodiment of the current invention. This can provide several possible application scenarios that previously required expensive, imprecise, or impractical hardware setups. For example, 3D ultrasound-based needle guidance.

Current sonographic procedures mostly use handheld 2D ultrasound (US) probes that return planar image slices through the scanned 3D volume (the "region of interest" (ROI)). For percutaneous interventions requiring tool guidance, prediction of the tool trajectory is currently based on tracking with sensors attached to the distal (external) tool end and on mental extrapolation of the trajectory, relying on the operator's experience. An integrated system with 3D ultrasound, tool tracking, tool trajectory prediction and interactive user guidance would be highly beneficial.

In one embodiment, an imaging device (e.g., ultrasound probe or an imaging probe with imaging sensors) may be removably coupled (e.g., attachable and/or detachable) to an optical head with a plurality of optical sensors (e.g., cameras) and a plurality of LEDs (e.g., infrared LEDs and/or visible light LEDs). The optical head may be in communication with a control unit. The control unit may receive images and/or data from the plurality of optical sensors. Based on this data, the control unit may determine a subset of optical sensors from the plurality of optical sensors to view one or more visible targets (e.g., instruments, environment, patient, and/or handheld devices, etc.). The selection of visible targets may depend on the current state of the system (e.g., programming on the control unit) and may include different targets over time. The images of the target may be transmitted from the optical sensors to the control unit and/or other imaging processing devices. The control unit may detect when one or more optical sensors from the subset of optical sensors is occluded or oriented in a direction away from the one or more visible targets. The control unit may transmit a warning (audio, visual, or haptic feedback) to an operator when the control unit detects that one or more of the subset of optical sensors are occluded or oriented in a direction away from the one or more visible targets. The control unit may determine a second subset of optical sensors from the plurality of optical sensors for viewing of the one or more visible targets when the control unit detects that one or more of the subset of optical sensors are occluded or oriented in a direction away from the one or more visible targets. The control unit may select a different subset of optical sensors from the plurality of optical sensors to optimize at least one of: a sampling rate, efficiency, and/or tracking performance. The control unit may query the subset of optical sensors at a higher bandwidth than optical sensors not in the subset of optical sensors. In an embodiment, the plurality of optical sensors includes three or more cameras. In another embodiment, the plurality of optical sensors includes eight cameras.

In one embodiment, a handheld device may contain a feedback system (e.g., haptic, audio, and/or visual) used to assist an operator in targeting. The handheld device may also enable position sensing. The feedback system may assist an operator in positioning a tool to or near a target. The feedback system may assist an operator in keeping an imaging device (e.g., an ultrasound probe) located at or above a target. For example, the feedback system may direct the operator to keep the imaging device at a viewing location for positioning a medical device (e.g., a needle) to a target. A control unit may determine an initial position and pose for an imaging device. The control unit may then determine if the imaging device is moving in the wrong direction (e.g., the operator of the imaging device is inadvertently sliding and/or rotating away from the region of interest) and/or if the imaging device is not or not quickly enough moving towards a target area. If the imaging device is not conforming to the target area, the control unit may transmit operator feedback to instruct the operator to move in a particular direction.

The feedback system may provide for spatial targeting enhancement when using a medical visualization/imaging system. The feedback system may include a directional haptic feedback device for handheld use (e.g., ungrounded haptic feedback) and a control unit for calculation of targeting information and resulting feedback control data. An embodiment may also include directional audio or visual feedback devices. In one embodiment a feedback device may contain any combination of haptic, audio, and/or visual feedback to the operator.

The haptic feedback device may include actuators for vibrotactile feedback, torque feedback, or both. The actuators may be designed and arranged in such a way as to enable transmission of directional haptic information ("haptic display") to the operator to provide instruction on positioning the device relative to some other object (e.g., external target locations or instrument positions).

The visual feedback may include arrows or animations on a screen. The audio feedback may include different tones and/or varying pitch to direct the operator to bring the imaging device or a medical tool to a determined location.

The feedback system may include a control unit that receives a target location relative to the device pose, or an instrument location relative to said target location, and computes the resulting device pose deviation. This pose deviation may be translated into haptic display actuations, audio feedback, and/or visual feedback. The haptic display actuations may include torque impulses for rotational deviation (e.g., generated by one or more linearly independent asymmetrical-impulse-driven flywheels), vibrotactile impulses for translational deviation (e.g., generated by one or more linearly independent asymmetric vibration actuators), or both. Depending on the application requirements, subsets of the full six degrees of freedom for haptic feedback may be realized in the device. The operator can then use the displayed directional information to position the haptic device in an ideal position that minimizes the device pose deviation in a closed-loop control fashion.

In one embodiment, the haptic feedback device may be mounted on a handheld ultrasound probe. Feedback actuations will thus result in, for example, haptic display that is directly calibrated to the operator's hand and the probe orientation. In another embodiment, the feedback device may be integrated into the handheld imaging device enclosure during manufacturing of the imaging device.

The haptic feedback device may contain sensing elements including one or more of accelerometers, gyroscopes, magnetometers, or optical sensors that provide pose and position information of the feedback device. In one embodiment, the haptic feedback device may be physically separate from the imaging device and the sensing elements may provide relative pose between the feedback device and the imaging device. The relative pose will transform the original pose deviation to feedback device coordinates, which then drives, for example, the haptic actuators. Such a physically separated haptic feedback device may be housed in, for example, a wrist-worn (e.g., a smartwatch), finger-worn, or forehead-worn housing.

In another embodiment, the feedback device can be mounted on an instrument to provide feedback (e.g., haptic, audio, and/or visual) to the operator. In one embodiment, one hand of the operator may be operating the imaging device and the other hand may be guiding an instrument, the feedback may assist the operator in guiding and/or placing the instrument relative to the imaging device or another external structure. For example, an operator may be operating an ultrasound probe to view images of a patient while receiving feedback on the placement of a needle to a target inside the patient.

In another application, the haptic feedback can be used to continuously position the imaging device along a time-varying path. The feedback may instruct an operator to move the imaging device, for example, back and forth over an area of the patient. Multiple images at slightly different angles will be acquired with the back and forth motion of the imaging device. These multiple images may be combined to produce a three-dimensional image of the target area.

FIG. 1 shows an embodiment of an imaging component 100 for an imaging system according to an embodiment of the current invention. Imaging component 100 includes an imaging device 110, bracket 120 that is structured to be attachable to imaging device 110. In the example of FIG. 1, the imaging device 110 is an ultrasound probe and bracket 120 is structured to be attached to a probe handle of the ultrasound probe. Ultrasound probes may include, for example, Ultrasonix #C5-2. However, the broad concepts of the current invention are not limited to only this example. The bracket 120 can be structured to be attachable to other handheld instruments for image-guided surgery, such as surgical orthopedic power tools or stand-alone handheld brackets, for example. In other embodiments, the bracket 120 can be structured to be attachable to the C-arm of an X-ray system or an MRI system, for example. In other embodiments, the bracket 120 may be missing to allow for handheld use of the imaging head.

Imaging component 100 may include top shell 180 and bottom shell 130 that may be coupled together to form a head shell. Top shell 180 and bottom shell 130 may be coupled securely to stabilization assembly 170 (e.g., stabilization bar). Head shell may house stabilization assembly 170 and other components of imaging component 100. Screws 190 may be used to couple the components of imaging component 100.

In one embodiment, head shell may also include a feedback device. The feedback device may be a haptic feedback device including, for example, one or more linearly independent asymmetrical-impulse-driven flywheels and/or one or more linearly independent asymmetric vibration actuators. Visual feedback may be shown on display 220 and may include, for example, arrows or on-screen animations. In another embodiment, one or more indicator LEDs may be used to provide visual feedback. Audio feedback may be provided through the use of, for example, one or more speakers.

In another embodiment, the feedback device may be separate from the head shell. The feedback device may be coupled to bracket 120 or may be removeably coupled to the imaging device through a separate fastener.

Imaging component 100 may also include one or more light-sensitive devices 150 (e.g., cameras, PSDs (position-sensitive devices), reflection-based laser sensing, etc.) securely attached to stabilization assembly 170. The one or more light-sensitive devices 150 may be at least one of a visible-light camera, an infra-red camera, a time-of-flight camera, a PSD (position-sensitive device), and/or a reflection-based laser sensing device in some embodiments of the current invention. The one or more light-sensitive devices 150 may be arranged to observe a surface region close to and during operation of the imaging component 100. In FIG. 1, the one or more light-sensitive devices 150 may be arranged and configured for stereo observation of a region of interest.

Imaging component 100 may also include a printed circuit board 140 that may include one or more microprocessors, one or more light sources, and a memory device. The light sources may include one or more LEDs, CFLs (compact fluorescent lamp), incandescent bulbs, and/or lasers. The light source may emit light in the visible spectrum, infrared, ultraviolet, and/or other spectrum. The printed circuit board may also be connected to one or more light-sensitive devices 150, the light source, and the memory device, and may be securely coupled to stabilization assembly 170.

Imaging component 100 may also include lens 160 that provides a screen for one or more light-sensitive devices 150. In one embodiment, lens 160 may be made of ultra-tough gorilla glass of 0.031" thickness. Lens 160 may be frosted or partially frosted to diffuse the light emitted from the light source.

Figure 2:
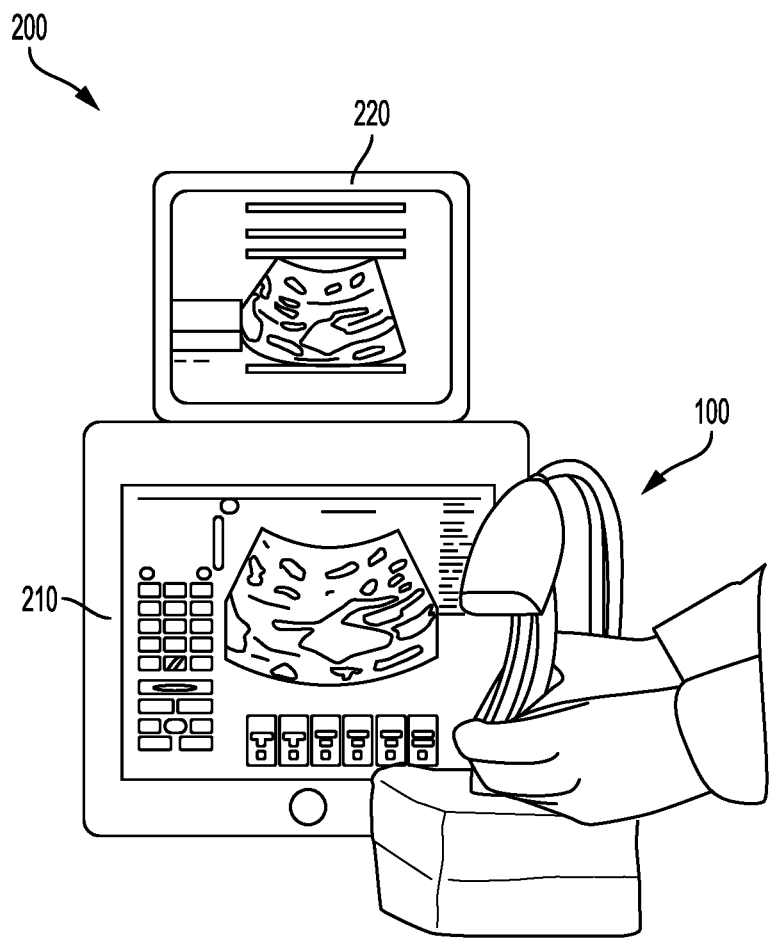
FIG. 2 shows another example of an imaging system.

FIG. 2 shows an embodiment of imaging system 200 (e.g., a medical imaging system) according to an embodiment of the current invention. Imaging system 200 includes imaging component 100 being controlled by a user. The user is also inserting a tool. Imaging system 200 includes image display 210. Image display may 210 display output from imaging device 110 such as sonogram images. Imaging system 200 also includes augmented display 220. Augmented display 220 may be a touch screen and allow input from the user. Augmented display 220 may overlay tracking information on top of output from imaging device 110.

Tracking information may include current tracking status, current location, and/or current insertion depth of the tool being inserted by the user. Overlaid information may also include tool tip location, tool tip distance to a selected target, and feedback information to help guide imaging device 110 and/or the insertion tool. Augmented display 220 may also provide visual feedback (e.g., arrows or animation) to direct the operator to reposition imaging device 110 and/or another medical tool. Augmented display 220 may include one or more speakers to provide audio feedback to the operator to assist in device and tool guidance.

In one embodiment, imaging system 200 may include, for example, an ultrasound probe (e.g., imaging device 110) and one or more displays (e.g., 210 and 220). A first display (e.g., 210) may be configured to communicate with the ultrasound probe to receive ultrasound signals and display images from the ultrasound probe. Imaging component 100 may be at least one of attached to or integral with the ultrasound probe and the imaging device may be configured to communicate with a second display (e.g., 220) to display images from the imaging component 100 and, in some embodiments, images from the ultrasound probe. The first and second display may be the same display. Similarly, the processing units that provide the data to be displayed on the one or more displays may be separate (two or more units) or integrated (one unit). The imaging component 100 may include stabilization assembly 170 (or other stabilization assembly), an imaging device assembly (e.g., 180 and 130) physically coupled to the stabilization assembly, a plurality of light-sensitive devices (e.g., 150) physically coupled to the stabilization assembly, and a memory unit (e.g., 440) physically coupled to the imaging device assembly (e.g., head shell). The memory unit may be configured to store calibration information and/or usage information for the image-guided ultrasound system.

Imaging system 200 may also include a control unit in communication with the feedback device. The control unit may be part of or coupled with the feedback device or the control unit may be separate from the feedback device. In one embodiment an operator may select a target on, for example, display 220. The control unit may receive the target selection. The control unit may also determine the position and pose of the feedback device, imaging device (e.g., ultrasound probe 110) and/or medical tools based on sensors connected to or outside the feedback device, the imaging device (e.g., ultrasound probe 110), and/or medical tools. The control unit may calculate the position and pose of the feedback device, imaging device (e.g., ultrasound probe 110) and/or medical tools to the target location. The control unit may determine if the feedback device, imaging device (e.g., ultrasound probe 110) and/or medical tools, for example, has moved away from the target position or is not or not quickly enough moving towards the target. The control unit may then calculate a deviation to another position and pose of the feedback device, imaging device (e.g., ultrasound probe 110) and/or medical tools. The control unit may translate the deviation into control data and transmit the control data to the feedback device. The feedback device can then instruct the operator to guide the feedback device, imaging device (e.g., ultrasound probe 110) and/or medical tools into the new position.

Figure 3:
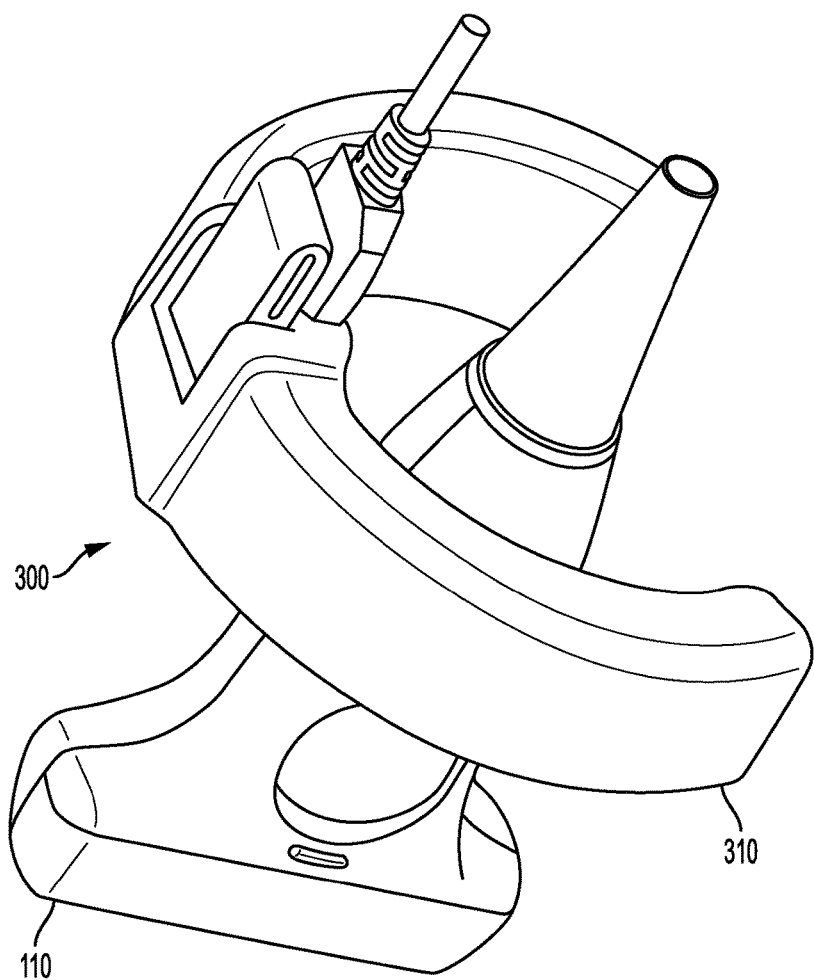
FIG. 3 illustrates an example enhanced optical head with an imaging device.

FIG. 3 illustrates an example enhanced optical head with an imaging device. Enhanced optical head 300 may include housing 310 that may house components such as one or more light-sensitive devices, feedback devices, memory devices, light sources, etc. Housing 310 (e.g., optical head assembly) of enhanced optical head 300 may be configured to be attachable to imaging device 110 (e.g., ultrasound probe). Housing 310 may be crescent-shaped or torus-shaped. Housing 310 may wrap completely or partially around the handle of imaging device 110. Imaging device 110 may be configured to accept a physical coupling with housing 310 and or enhanced optical head 300.

Figure 4:
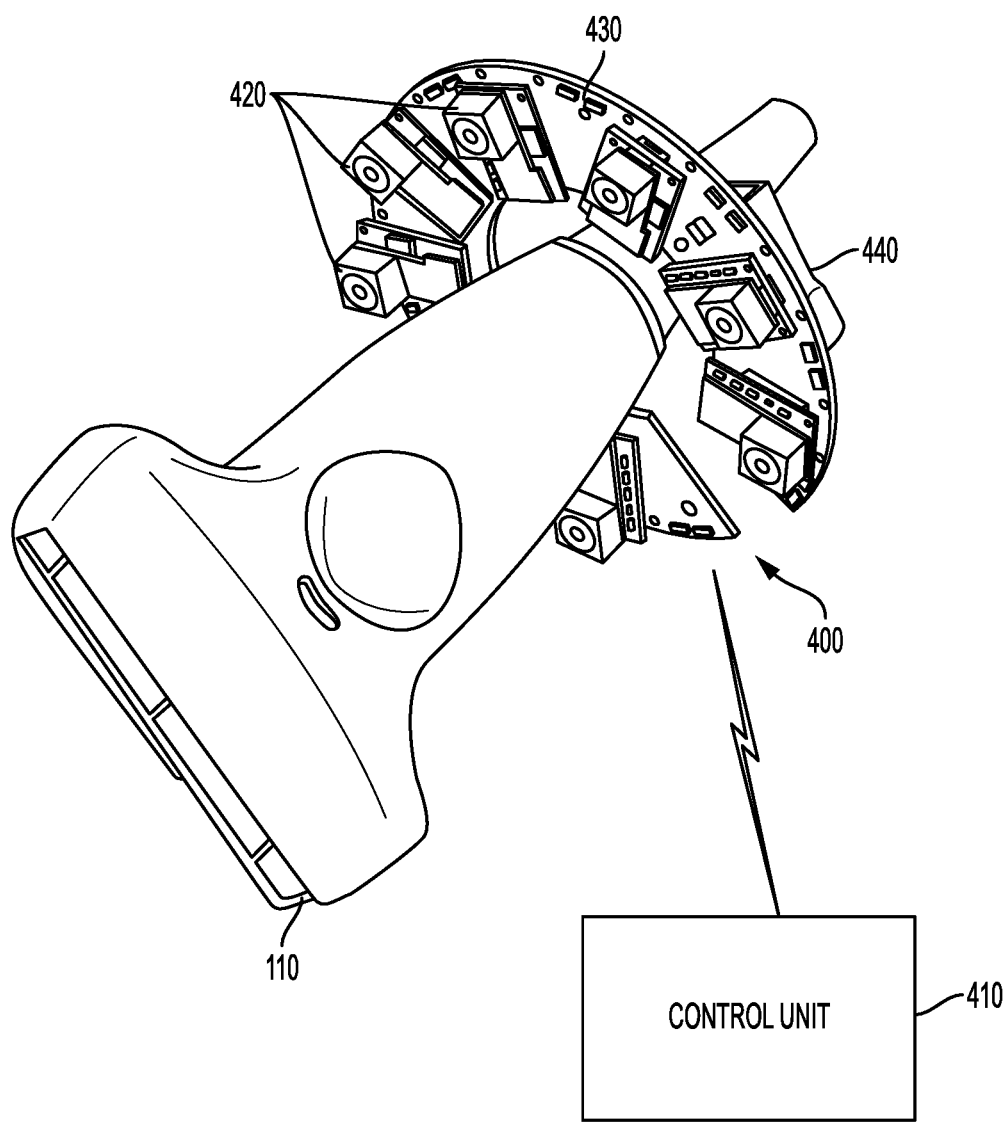
FIG. 4 shows a perspective view of imaging components for an enhanced optical head.

FIG. 4 shows example imaging components for an enhanced optical head. FIG. 4 shows optical carrier unit 400 (e.g., printed circuit board (PCB)) that may be housed in housing 310 and/or be a component of enhanced optical head 300 which may be connected to imaging device 110. Optical carrier unit 400 may be crescent-shaped or torus-shaped.

Enhanced optical head 300 may provide multi-directional or panoramic tracking of one or more of instruments, environment, patient, or handheld device. Enhanced optical head 300 may be in communication (wired or wireless) with control unit 410.

FIG. 4 depicts eight optical sensors 420 (e.g. video cameras) but more cameras or fewer cameras may be implemented. For example, carrier unit 400 may include two or more (e.g., a plurality) optical sensors 420 (e.g., cameras or light sensing devices). Optical sensors 420 may be arranged radially on carrier unit 400. The carrier unit 400 exhibiting a stabilization property to maintain the relative arrangement of optical sensors 420 around a handheld imaging device 110 (e.g. an ultrasound probe). Optical sensors 420 may observe the neighborhood of the imaging device 110. FIG. 4 also shows interfacing electronics to drive and communicate with the sensors.

Carrier unit 400 may also include one or more illumination sources 430 (e.g., IR LEDs or visible light LEDs). Illumination sources 430 may be oriented generally in the same direction as optical sensors 420. By arranging multiple lighting sources 430 in the generally same direction, a diffusion effect is achieved which serves to blur shadowing artifacts. The optical sensors 420 may point in different directions and may transmit different views of the same object or objects. Optical sensors 420 may transmit data and/or images to control unit 410 for processing. Control unit 410 may transmit configuration data to the optical sensors 420. Memory unit 410 may be a storage facility that may contain calibration, usage, and/or licensing data/information for the optical head 300 and/or imaging system 200.

In one embodiment, a subset of the optical sensors may observe the environment of the enhanced optical head 300 and transmit captured images to control unit 410. Control unit 410 may extract relevant information from the images and select a new subset of optical sensors 420 based on at least one of current observations and the observation history.

In one embodiment, the optical sensors may be arranged in such ways that at any time some subset of optical sensors 420 may be occluded or oriented in a direction that does not allow observation of relevant information. Control unit 410 may then select a different subset of optical sensors 420 to optimize one or more of sampling rate, system efficiency, or tracking performance.

In another embodiment, the viewing volumes of some optical sensors may be partially overlapping, thus allowing for stereo or multi-sensor observations of the same external features. Control unit 410 may select subsets of optical sensors to one or more of sampling rate, system efficiency, or tracking performance at least for one or more of improved robustness or accuracy. This selection may be based on external feature locations estimated from current or previous observations.

Enhanced optical head 300 may be placed high on the imaging device 110 (e.g., away from the ultrasound transducer) and the plurality of optical sensors may provide a wide view of the one or more visible targets but at reduced accuracy. This may be useful if long medical tools are being used (e.g., large needles). In another embodiment, enhanced optical head 300 may be placed low on the imaging device 110 (e.g., towards the ultrasound transducer) and the plurality of optical sensors may provide an accurate view of the one or more visible targets but at a reduced view. This may be useful if small medical tools are being used (e.g., short needles).

In one embodiment, control unit 410 may receive images from two or more optical sensors of the plurality of optical sensors 420 where the images partially overlap providing stereo or multi-sensor observations of one or more features (e.g., certain features). As described in Wang, "The Kinect as an Interventional Tracking System," SPIE 2012, herein incorporated by reference in its entirety, these multi-sensor observations may be used to reconstruct the 3D pose of targets relative to the optical head 300. Although the reference describes stereo reconstruction in particular, those skilled in the art will readily understand the extension to multi-camera (e.g., optical sensors 420) reconstruction.

Control unit 410 may be configurable to determine the number of cameras or optical sensors 420 from which to receive images. The more cameras, the more robust the system and the more false positives. The fewer number of cameras, the more accurate and the less robust.

Figure 5:
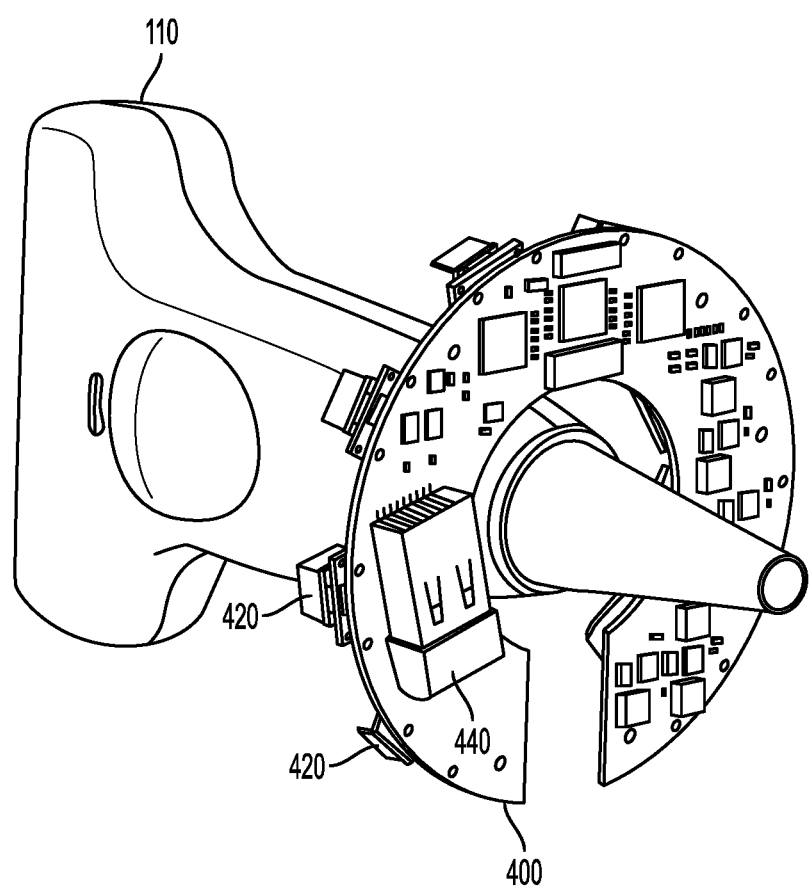
FIG. 5 shows another perspective view of imaging components for an enhanced optical head.

FIG. 5 shows another perspective view of imaging components for an enhanced optical head. Optical sensors 420 may be coupled to optical carrier unit 400 (e.g., printed circuit board (PCB)). The plurality of optical sensors 420 may be spaced evenly apart and transmit a plurality of images to control unit 410. Optical sensors 420 may be configured to receive instructions from control unit 410. The instructions may include adjusting the imaging bandwidth for each individual optical sensor of the plurality of optical sensors 420. A plurality of LEDs 430 may be included in housing 310 and may be coupled to optical carrier unit 400. LEDs 430 may be in communication with control unit 410. Optical carrier unit 400 may also include memory 440. Control unit 410 may be in communication with memory 440.

Memory 440 may include one or more of calibration, usage, and/or licensing data. Calibration data may include camera calibration for single cameras, stereo or multi-camera calibration for suitable subsets of cameras, or an overall n-camera calibration matrix for all cameras simultaneously. Such calibration data may be described in Zhang Z, "A flexible new technique for camera calibration," 2000, IEEE Transactions on Pattern Analysis and Machine Intelligence, which is herein incorporated by reference in its entirety. Usage data may include times and durations of system use, as determined by one or more of a real-time clock on the optical head, the control unit clock, and/or some other time measurement method. Licensing data may include one or more of remaining licensed use time and/or a fixed pre-scheduled expiration date.

In one embodiment, simultaneous long-axis ultrasound imaging and continuous transverse (short-axis) reconstruction in a central region of interest of the imaging area may be provided. Enhanced optical head 300 may include a mounted sensing device. Sensing device may include sensing elements able to detect imaging device 110 pose relative to a reference pose. The sensing elements may include internal or external optical sensors, inertial sensors, ultrasound-image-based pose estimation, attached markers (for an external tracking system), or a combination.

Figure 6:
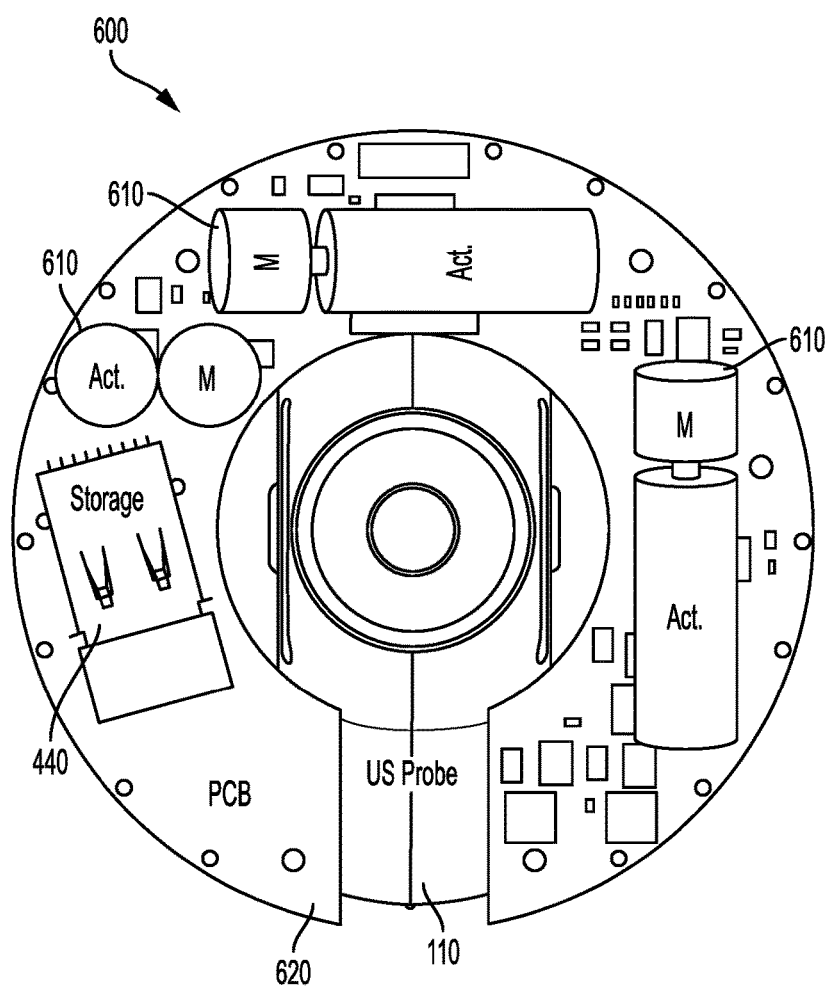
FIG. 6 shows example torque actuator components on a feedback device.

FIG. 6 shows example torque actuator components on an example feedback device 600. Torque actuators 610 (shown as cylinders labeled "Act," with actuated masses "M") are arranged with their respective supporting electronics components on a printed circuit board 620. Printed circuit board 620 may be the same board as carrier unit 400, may be in combination, or they may be separate. Feedback device 600 may generally have the same overall shape as the optical head components, in order to minimize the physical footprint of the combination. Feedback device 600 may be close to or around imaging device 110. The specific spatial configuration of torque actuators 610 may be dictated by requirements on the degrees of freedom of actuation, i.e. with directions of actuation aligned such that they are non-collinear where multiple degrees of freedom are needed. One possible way to achieve this would be to arrange the motor axes of up to three torque actuators 610 perpendicular to each other, with each axis defining a degree of freedom for torque actuation. Printed circuit board 620 may also include memory unit 440. Memory unit 440 may be configured to store calibration information and/or usage information.

Figure 7:
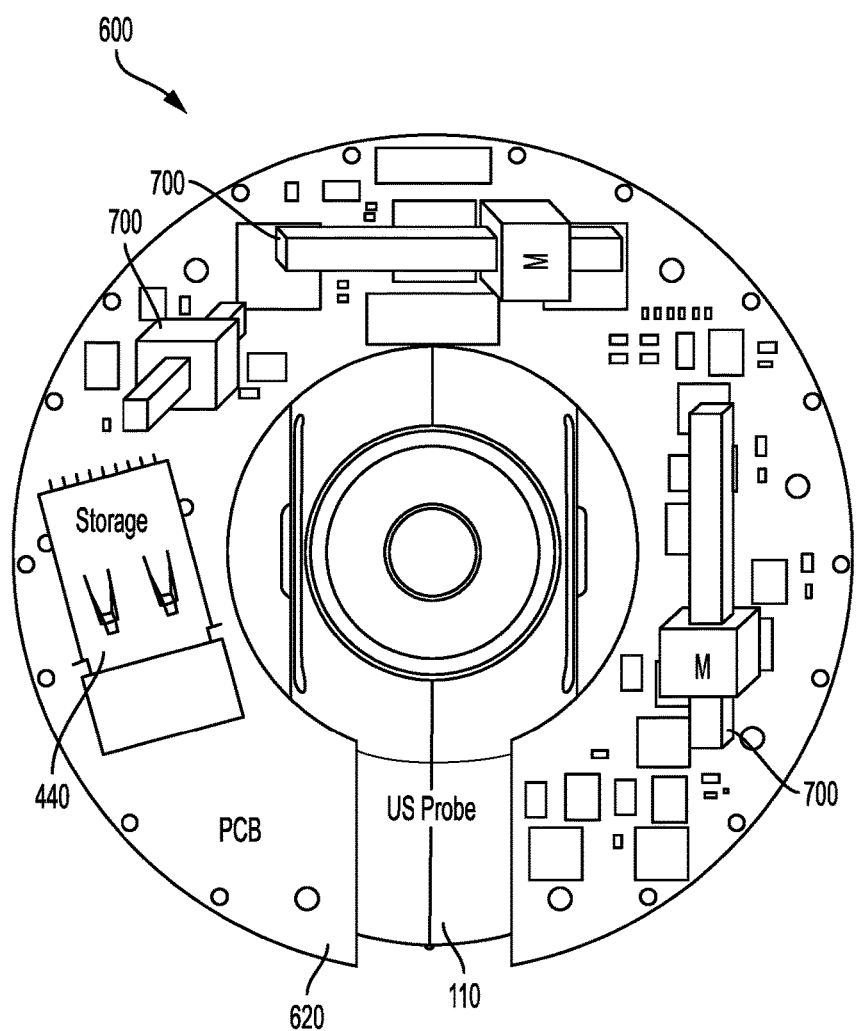
FIG. 7 shows example vibrotactile components on a feedback device.

FIG. 7 shows example vibrotactile components on example feedback device 600. Vibrotactile actuators 700 (shown as cylinders labeled "Act," with actuated masses "M") are arranged with their respective supporting electronics components on printed circuit board 620 close to or around imaging device 110. The specific spatial configuration of vibrotactile actuators 700 may be dictated by requirements on the degrees of freedom of actuation, i.e. with directions of actuation aligned such that they are non-collinear where multiple degrees of freedom are needed. One possible way to achieve this would be to arrange the motor axes of up to three vibrotactile actuators 700 perpendicular to each other, with each axis defining a degree of freedom for vibrotactile actuation. Vibrotactile actuators 700 may be combined with torque actuators 610.

Although FIGS. 1-7 illustrate the imaging system as an ultrasound imaging system and that the bracket 120 is structured to be attached to an imaging device 110 as an ultrasound probe, the broad concepts of the current invention are not limited to this example. The bracket may be structured to be attachable to other imaging systems, such as, but not limited to, x-ray and magnetic resonance imaging systems, for example.

Figure 8:
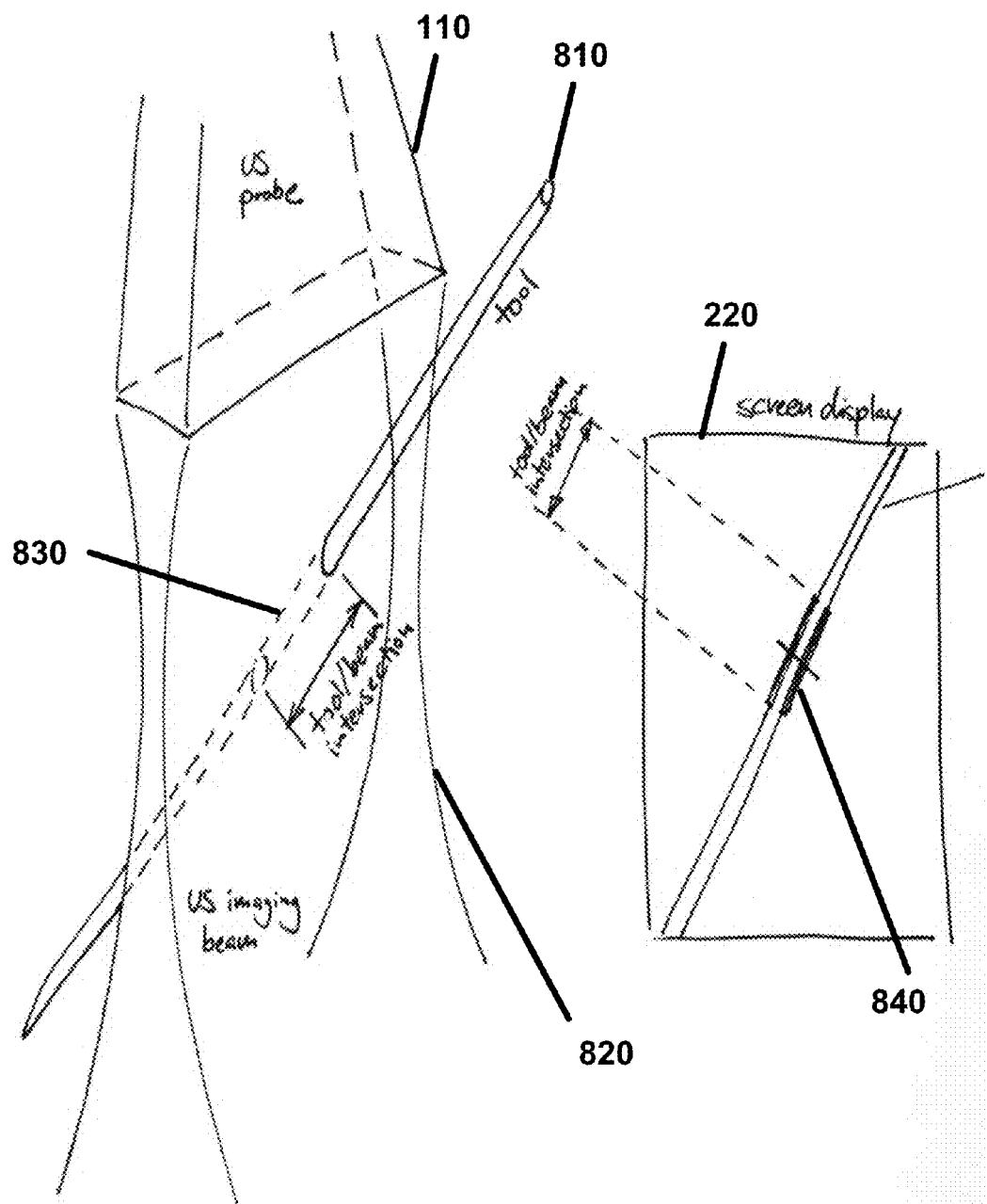
FIG. 8 illustrates an intersection of a tool and an ultrasound beam.

FIG. 8 illustrates the intersection of a tool 810 and ultrasound beam 820 from imaging device 110 as an ultrasound probe. The image processing module may execute instructions for tracking a medical tool 810 (e.g., a needle, a pointer, a biopsy tool, a laparoscope, an ablation device, a surgical instrument, or an elongated tool). Image processing module may first register the tool with the imaging device, where the position of the tool 810 is known with respect to the imaging device. A representation of tool 810 may be presented on display 220. The processing module may receive a selection of a target (e.g., a tumor, a vessel, a suspicious lesion, or other clinically relevant sites) in the images from the ultrasound probe, or may receive the target selection based on other imaging data introduced into the system (such as pre-defined target sites in CT or MRI data, later to be registered to the imaging device). The selection may be received from a touchscreen displaying the ultrasound images, for example. The module may also track the tool, display a representation of the tool in the display as the tool is being tracked; indicate a tool tip in the display (e.g., though the use of one or more perpendicular lines, pointed line arrangements, and/or color variations); calculate a distance between the tool tip and the target; output audio, wherein the audio changes based on the calculated distance between the tool tip and the target; display the calculated distance between the tool tip and the target; output visual cues as to the quality of the tool tracking; and/or indicating a loss of tool tracking though audio or visual cues. The processing module may further display the tracked tool as a line; and may represent the quality of the tool tracking as a function of a length of the displayed line. In a specific example of a tracked tool 810 intersecting the ultrasound imaging area at 830, there may be a certain segment of the tool 810 physically contained within the volume of the ultrasound beam 820. The length of this segment can be computed by the processing module based on knowledge about the standard beam shape, and may be displayed as overlaid variations in color or length or as overlaid markers 840 on the displayed tool representation itself.

Figure 9:
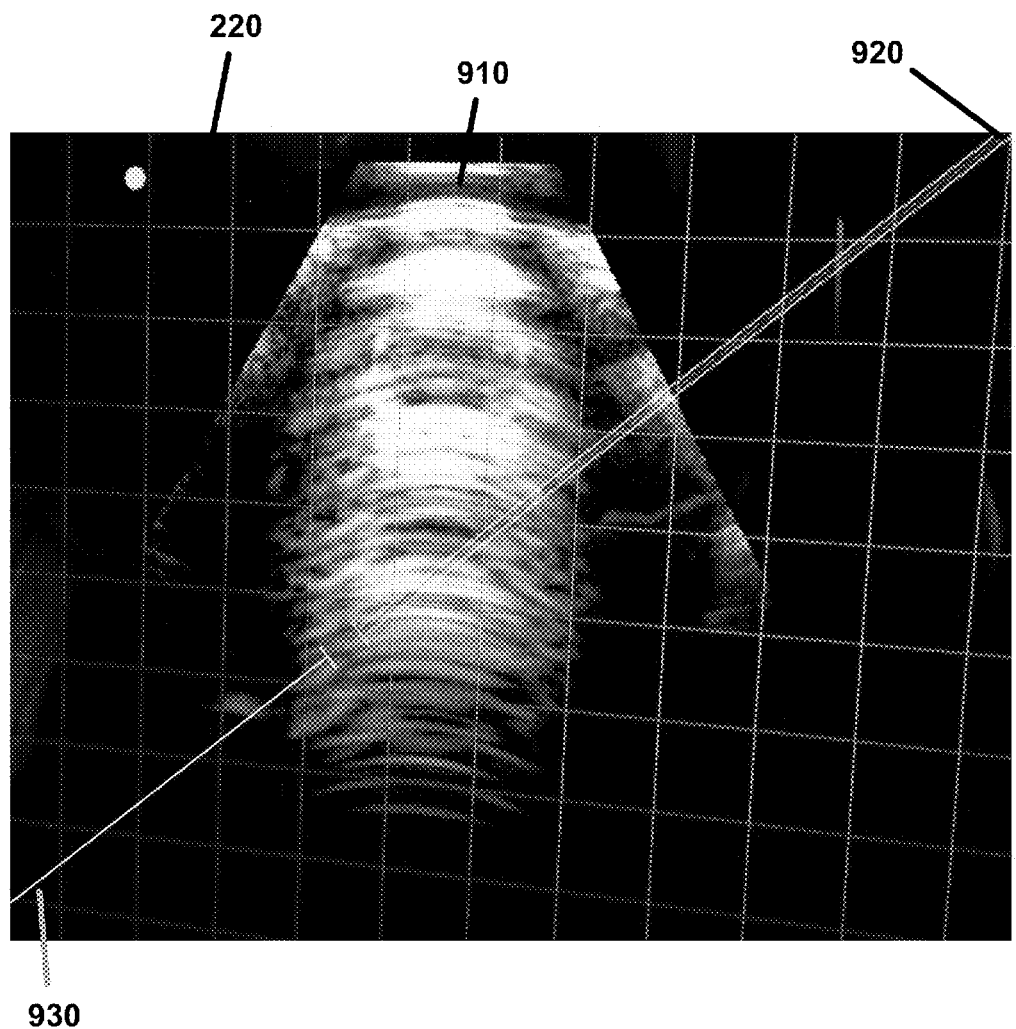
FIG. 9 shows an example screenshot of a tool-tip display.

FIG. 9 shows an example screenshot of a tool-tip display according to an embodiment of the current invention. FIG. 9 includes a screen shot from display 220 including ultrasound images 910. Display 220 also shows a representation of the medical tool 920 indicating the tool's 810 current position (indicated in FIG. 9 by long perpendicular lines (e.g., double green lines)) including the tip (indicated in FIG. 9 by short perpendicular lines) and a single line indicating the predicted trajectory 930.

Figure 10:
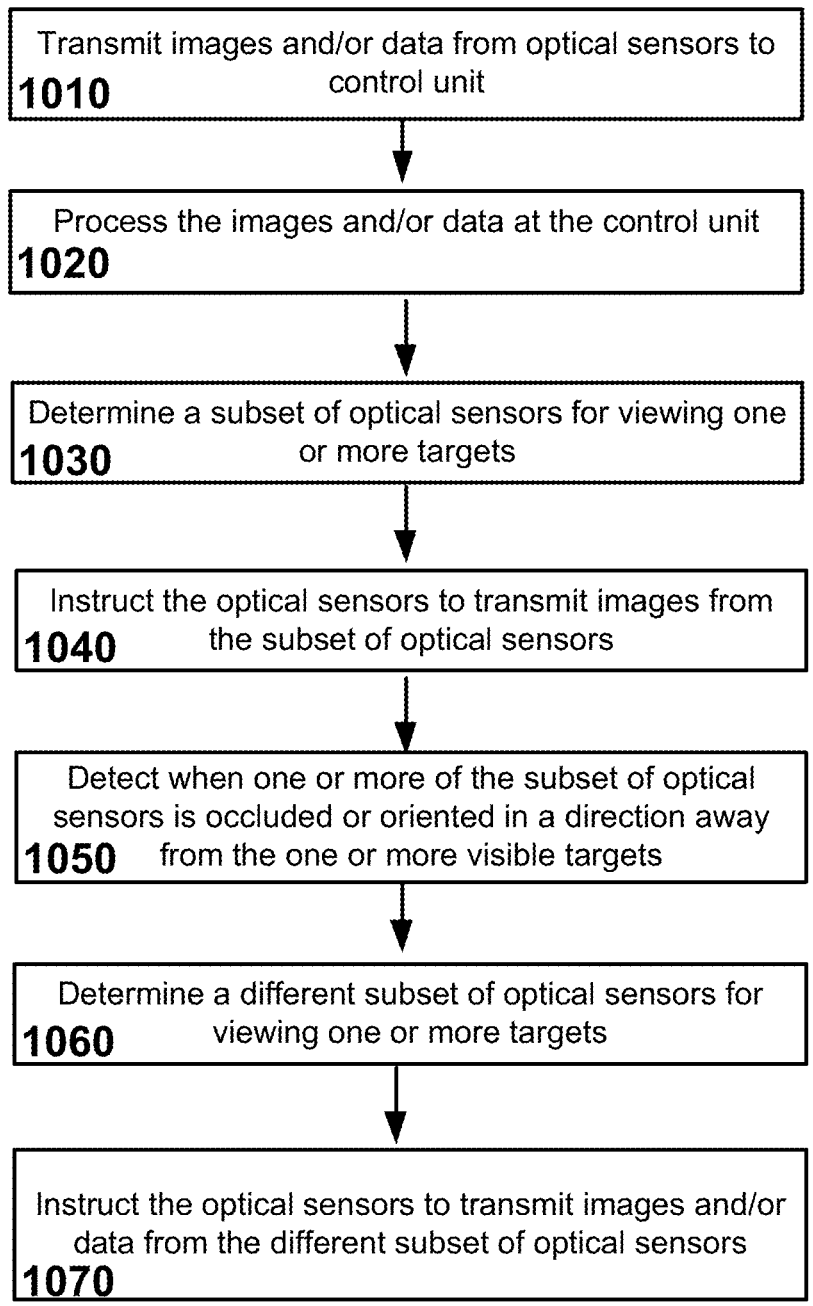
FIG. 10 depicts an example workflow.

FIG. 10 depicts an example workflow according to an embodiment of the current invention. In 1010, images and/or data may be transmitted from optical sensors 310 to control unit 320. From 1010, flow may move to 1020.

In 1020, control unit 410 may process the received images and/or data from the optical sensors 310. This may be accomplished as described in Wang, "The Kinect as an Interventional Tracking System," SPIE 2012, which is herein incorporated by reference in its entirety. For example, control unit 410 may execute the algorithm described by Wang on adjacent stereo pairs of optical sensors, or on single optical sensors, to locate instruments in these images or data streams. The programing of control unit 410 may then determine that relevant targets are only visible from a subset of optical sensors. From 1020, flow may move to 1030.

In 1030, control unit 320 may determine a subset of optical sensors from the optical sensors 310 to view one or more visible targets. This determination may be based on the steps in 1020. In addition, optical sensors whose viewing volumes are adjacent to these determined to contain targets of interest in 1020 may be included in this subset. From 1030, flow may move to 1040.

In 1040, control unit 320 may instruct the determined subset of optical sensors from the optical sensors 310 to transmit images. In one embodiment, the determined subset may have a faster refresh rate than the non-subset optical sensors. From 1040, flow may move to 1050.

In 1050, control unit 410 may detect when one or more of the subset of optical sensors is occluded or oriented in a direction away from the one or more visible targets. For example, the operator's hand may be blocking the cameras. Control unit 410 may determine that one or more cameras are occluded or oriented in a direction away from the one or more visible targets. The determining may be based on one or more of the following approaches: detection of partially occluded observations of targets in these cameras, temporal knowledge about previous observation of targets in these cameras, local spatial knowledge about relative motion of targets through the set of cameras, global spatial knowledge about presence or location targets relative to the cameras, detection of known occluding objects based on prior information about their appearance, detection of unknown occluding objects based on prior information about the targets' appearance, or combinations of the above. In one embodiment, control unit 410 may issue a warning to the operator that a camera is occluded or oriented in a direction away from the one or more visible targets. The warning may be audio (e.g., a beep), visual (e.g., on display 220, or visible LEDs), or via haptic feedback (e.g., the imaging device vibrates). From 1050, flow may move to 1060.

In 1060, control unit 410 may determine a different subset of optical sensors from the plurality of optical sensors 420 to view the one or more visible targets. The determining may be based on one or more of the following approaches: knowledge about geometric adjacency between the optical sensors' viewing volumes and extrapolation of expected target locations from known target motion; random, pseudorandom, or deterministic cycling through the set of optical sensors; heuristic selection based on statistical or process-based information about expected target locations; detection of targets in non-subset optical sensors operating at lower bandwidths; and/or no changes of the subset. From 1060, flow may move to 1070.

In 1070, control unit 320 may instruct the determined different subset of optical sensors from the plurality of optical sensors 310 to transmit images and/or data. In one embodiment control unit 320 may transmit bandwidth instructions to the plurality of optical sensors 310 based on the determined subset of optical sensors (e.g., the determined different subset may transmit at a higher bandwidth than the other optical sensors).

In an embodiment, tracking of a medical tool (e.g., needle, surgical instrument) may be accomplished through one or more visible features on the tool. (Basic tool tracking has been described in previous publications by the inventors, such as Stolka et al. "Navigation with local sensors in handheld 3D ultrasound: initial in-vivo experience," SPIE Medical Imaging 2011, Lake Buena Vista, Fla./USA, pp. 79681J-79681J. International Society for Optics and Photonics, 2011, and Wang et al. "The Kinect as an interventional tracking system," SPIE Medical Imaging, San Diego, Calif., USA, pp. 83160U-83160U. International Society for Optics and Photonics, 2012, both of which are included by reference in their entirety.) The visible feature may include a detectable pattern, the pattern being initially created using a pseudo random binary sequence, or more generally a de Bruijn sequence, wherein the pattern is one of marked, printed, etched, or applied to the tool. The pattern may be used to detect insertion depth of the tool into a human or animal body. Alternatively, the visible feature may include an attachment such as a ring attached to the tool. The ring may be reflective and/or cylindrical or handle shaped. The ring may include a detectable pattern used in calculating an insertion depth of the tip of the tool, the detectable pattern may be initially created using a pseudo random binary sequence. Imaging system 200 may initially calculate a distance from the ring to the tip of the tool and use this calculated distance to calibrate the imaging system 200 for tool tracking.

The displayed information to assist in medical tool positioning may include information about the length of intersection between the medical tool and the non-infinitesimally thin ultrasound imaging plane, by drawing markers on the medical tool line to denote the extent of said intersection. In other words, a line may indicate the medical tool trajectory, wherein a portion of the line may be shaded differently to indicate the area where the medical tool will cross the imaging plane of the ultrasound Insertion depth calculation may be made based on the one or more visible features on the tool. Because of the nature of the visible feature, the insertion depth of the tip of the tool may be correctly calculated even when a portion of the one or more visible features is not viewable by the one or more light sensitive devices. For example, when the visible feature includes the detectable pattern created using a pseudo random binary sequence, the pattern is non-periodic and unique over small segments. Therefore, even if a small portion of the pattern is visible, imaging system 200 may still calculate the insertion depth. Tool tip location may be calculated (e.g., candidate tip locations) using the one or more visible features. The calculated tip locations may be in a three dimensional plane and may be based on the insertion location, calculated insertion depth, and angle of entry of the medical tool. Insertion depth of the tool tip and possible tip locations may be displayed on augmented display 220. A surgeon or other medical personnel may use the displayed information when performing an IGI, for example.

The following describes one possible technique of localizing the medical tool tip in stereo images using the pattern on the medical tool shaft in an embodiment. Given a pair of stereo images (left and right light-sensitive device images) and light-sensitive device calibration (intrinsic and extrinsic light-sensitive device parameters), the first step of tip localization is to rectify the left and right images. Next, the medical tool is detected in these images as straight lines centered at the middle of the shaft. In order to localize the tip of the medical tool in 3D, the medical tool line is reconstructed in 3D space. This line is then sampled with a constant delta providing a set of 3D points. These points are then projected back into the left and right images resulting in two sets of 2D points for the left and right rectified images. Then, the pixel intensities at these points are computed using interpolation. This will generate two intensity vectors with regular sampling. In the next step, the two intensity vectors are correlated against all possible "sub-patterns". A sub-pattern is a minimal continuous portion of the whole pattern that could be uniquely identified. For each sub-pattern, the location that maximizes correlation and the correlation value is recorded. The sub-patterns with the highest correlation value are selected in the left and right vectors. Since the offset of the sub-pattern with respect to the tip is known, the 3D location of the tip can be estimated. Note that left and right images provide two almost independent estimates of the tip location. As a verification step, the two estimated tip locations should be closer than a threshold. The final tip location is given as the weighted-average of these two estimated tip positions.

In another embodiment, light waves may be filtered by the one or more light sensitive devices to only allow light of a specific wavelength and to restrict light of other wavelengths. A coating may be applied to the medical tool or other tool that may be illuminated based on receiving light of a specific wavelength. The coating may produce or reflect a light of the specific wavelength. The reflected or produced light of a specific wavelength may be detected by the light sensitive devices. The reflected or produced light of a specific wavelength may reduce the occurrence of false positives. Further, the coating may only illuminate or produce light of a specific wavelength to reveal the detectable pattern. The possible tip locations and insertion depth of the tip of the medical tool or tool may be calculated based on based on the displayed detectable pattern of light in a specific wavelength.

Illustrative Computer System

Figure 11:
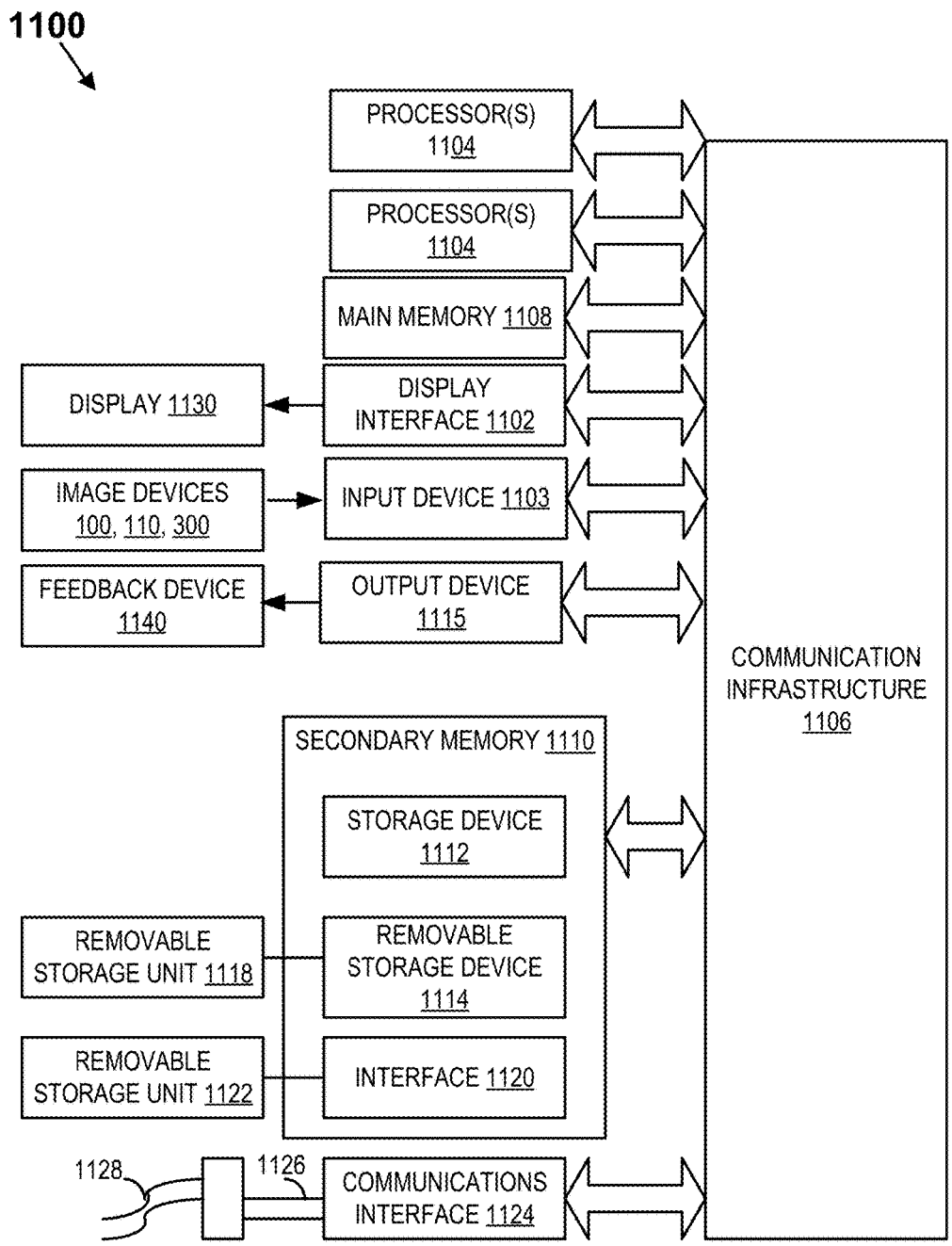
FIG. 11 depicts an illustrative embodiment of a computer for performing the methods and building the systems and performing the methods described herein.

FIG. 11 depicts an illustrative computer system that may be used in implementing an illustrative embodiment of the present invention. Specifically, FIG. 11 depicts an illustrative embodiment of a computer system 1100 that may be used in computing devices such as, e.g., but not limited to, standalone or client or server devices. FIG. 11 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 1100 is shown in FIG. 11, depicting an illustrative embodiment of a block diagram of an illustrative computer system useful for implementing the present invention. Specifically, FIG. 11 illustrates an example computer 1100, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/Windows 8, etc. available from MICROSOFT® Corporation of Redmond, Wash., U.S.A. or an Apple computer or tablet executing MAC® OS, OS X, or iOS from Apple® of Cupertino, Calif., U.S.A., or a computer running a Linux or other UNIX derivative. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 1100 is shown in FIG. 11. Other components of the invention, such as, e.g., (but not limited to) a computing device, a communications device, a telephone, a personal digital assistant (PDA), an iPhone, an iPad, a Surface, and Android device, a 3G/4G wireless device, an LTE device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 11. In an illustrative embodiment, services may be provided on demand using, e.g., an interactive television device (iTV), a video on demand system (VOD), via a digital video recorder (DVR), and/or other on demand viewing system. Computer system 1100 and/or parts of computer system 1100 may be used to implement the network, processing device, and/or components as described in FIGS. 1-7. Such as imaging component 100, printed circuit board 140, and/or other devices of imaging system 200.

The computer system 1100 may include one or more processors, such as, e.g., but not limited to, processor(s) 1104. The processor(s) 1104 may be connected to a communication infrastructure 1106 (e.g., but not limited to, a communications bus, cross-over bar, interconnect, or network, etc.). Processor 1104 may include any type of processor, microprocessor, or processing logic that may interpret and execute instructions (e.g., for example, a field programmable gate array (FPGA)). Processor 1104 may comprise a single device (e.g., for example, a single core) and/or a group of devices (e.g., multi-core). The processor 1104 may include logic configured to execute computer-executable instructions configured to implement one or more embodiments. The instructions may reside in main memory 1108 or secondary memory 1110. Processors 1104 may also include multiple independent cores, such as a dual-core processor or a multi-core processor. Processors 1104 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 1100 may include a display interface 1102 that may forward, e.g., but not limited to, graphics, text, and other data, etc., from the communication infrastructure 1106 (or from a frame buffer, etc., not shown) for display on the display unit 1130. The display unit 1130 may be, for example, a television, a computer monitor, iPad, and/or a mobile phone screen. The output may also be provided as sound through a speaker.

The computer system 1100 may also include, e.g., but is not limited to, a main memory 1108, random access memory (RAM), and a secondary memory 1110, etc. Main memory 1108, random access memory (RAM), and a secondary memory 1110, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 1110 may include, for example, (but is not limited to) a hard disk drive 1112 and/or a removable storage drive 1114, representing a floppy diskette drive, a magnetic tape drive, an optical disk drive, a compact disk drive CD-ROM, flash memory, etc. The removable storage drive 1114 may, e.g., but is not limited to, read from and/or write to a removable storage unit 1118 in a well-known manner. Removable storage unit 1118, also called a program storage device or a computer program product, may represent, e.g., but is not limited to, a floppy disk, magnetic tape, optical disk, compact disk, etc. which may be read from and written to removable storage drive 1114. As will be appreciated, the removable storage unit 1118 may include a computer usable storage medium having stored therein computer software and/or data. Secondary memory 1210 may also include memory unit 440.

In alternative illustrative embodiments, secondary memory 1110 may include other similar devices for allowing computer programs or other instructions to be loaded into computer system 1100. Such devices may include, for example, a removable storage unit 1122 and an interface 1120. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1122 and interfaces 1120, which may allow software and data to be transferred from the removable storage unit 1122 to computer system 1100.

Computer 1100 may also include an input device 1103 which may include any mechanism or combination of mechanisms that may permit information to be input into computer system 1100 from, e.g., a user. Input device 1103 may include logic configured to receive information for computer system 1100 from, e.g. a user. Examples of input device 1103 may include, e.g., but not limited to, a mouse, pen-based pointing device, or other pointing device such as a digitizer, a touch sensitive display device, and/or a keyboard or other data entry device (none of which are labeled). Other input devices 1103 may include, e.g., but not limited to, a biometric input device, a video source, an audio source, a microphone, a web cam, a video camera, a light-sensitive device, and/or other camera. Input device may include imaging device 110, imaging component 100, and enhanced optical head 300.

Computer 1100 may also include output devices 1115 which may include any mechanism or combination of mechanisms that may output information from computer system 1100. Output device 1115 may include logic configured to output information from computer system 1100. Embodiments of output device 1115 may include, e.g., but not limited to, display 1101, and display interface 1102, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Output device 1115 may include feedback device 1140. Feedback device 1140 may include haptic, audio, and/or visual feedback.

Computer 1100 may include input/output (I/O) devices such as, e.g., (but not limited to) input device 1103, communications interface 1124, cable 1128 and communications path 1126, etc. These devices may include, e.g., but are not limited to, a network interface card, and/or modems.

Communications interface 1124 may allow software and data to be transferred between computer system 1100 and external devices.

In this document, the terms "computer program medium" and "computer readable medium" may be used to generally refer to media such as, e.g., but not limited to, removable storage drive 1114, a hard disk installed in hard disk drive 1112, memory unit 440, flash memories, removable discs, non-removable discs, etc. In addition, it should be noted that various electromagnetic radiation, such as wireless communication, electrical communication carried over an electrically conductive wire (e.g., but not limited to twisted pair, CATS, etc.) or an optical medium (e.g., but not limited to, optical fiber) and the like may be encoded to carry computer-executable instructions and/or computer data that embodiments of the invention on e.g., a communication network. These computer program products may provide software to computer system 1100. It should be noted that a computer-readable medium that comprises computer-executable instructions for execution in a processor may be configured to store various embodiments of the present invention. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application. It may also be part of a system for detecting network coverage and responsiveness. A general purpose computer may be specialized by storing programming logic that enables one or more processors to perform the techniques indicated herein and the steps of, for example, FIG. 10.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents.

We claim:

1. A medical imaging system comprising:
an imaging device;
an optical head coupled to the imaging device, the optical head comprising a plurality of optical sensors; and
a control unit in communication with the optical head, the control unit configured to:
receive data from the plurality of optical sensors,
determine a subset of optical sensors from the plurality of optical sensors for viewing one or more visible targets based on the received data from the plurality of optical sensors, and
instruct the optical head to transmit images from the subset of optical sensors.

2. The system of claim 1, wherein the one or more visible targets include at least one of: one or more instruments, an environment, a patient, or a handheld device.

3. The system of claim 1, wherein the imaging device is an ultrasound probe.

4. The system of claim 1, wherein the plurality of optical sensors comprises at least three cameras.

5. The system of claim 1, wherein the control unit:
detects when one or more optical sensors from the subset of optical sensors is occluded or oriented in a direction away from one or more of the visible targets; and
determines a second subset of optical sensors from the plurality of optical sensors for viewing of one or more of the visible targets based on the received data from the plurality of optical sensors.

6. The system of claim 1, wherein the control unit transmits a warning to an operator when the control unit detects that one or more of the subset of optical sensors are occluded from one or more of the visible targets.

7. The system of claim 1, wherein the control unit selects a different subset of optical sensors from the plurality of optical sensors to optimize at least one of: a sampling rate, efficiency, or tracking performance.

8. The system of claim 1, wherein the control unit queries the subset of optical sensors at a higher bandwidth than optical sensors not in the subset of optical sensors.

9. The system of claim 1, wherein images from two or more optical sensors of the plurality of optical sensors partially overlap providing stereo or multi-sensor observations of one or more features.

10. The system of claim 1, further comprising: a memory unit in communication with the optical head, the memory unit configured to store at least one of calibration information or usage information for the medical imaging system.

11. The system of claim 1, wherein the optical head is attachable on and detachable from the imaging device.

12. An optical tracking device comprising:
a housing configured to be attachable to an ultrasound probe;
a printed circuit board (PCB) housed in the housing; and
a plurality of optical sensors coupled to the PCB, the plurality of optical sensors configured to transmit a plurality of images to a control unit, the plurality of optical sensors configured to receive instructions from the control unit, the instructions including configuration data to adjust bandwidth for communication between the plurality of optical sensors and the controller.

13. The optical tracking device of claim 12, wherein the housing is one of crescent-shaped or torus-shaped and the PCB is crescent-shaped, when the housing is crescent-shaped, or torus-shaped, when the housing is torus-shaped.

14. The optical tracking device of claim 12, further comprising:
a plurality of infrared LEDs.

15. The optical tracking device of claim 12, further comprising:
a memory device storing at least one of calibration data or usage data.

16. The optical tracking device of claim 12, further comprising:
a haptic feedback device coupled to the housing.

17. The optical tracking device of claim 12, wherein the plurality of optical sensors comprises at least three cameras.

18. The optical tracking device of claim 12, wherein the plurality of optical sensors are spaced evenly apart.

19. An imaging device comprising:
an imaging probe comprising an imaging sensor and a handle;
an optical head assembly configured to be attachable and detachable to the handle of the imaging probe; and
a plurality of optical sensors coupled to the optical head assembly, wherein the plurality of optical sensors are in communication with a control unit, the control unit configured to:

receive image data from the plurality of optical sensors, determine a subset of optical sensors from the plurality of optical sensors for viewing one or more visible targets, and transmit instructions including configuration data to adjust bandwidth for communication between the plurality of optical sensors and the controller.

20. The imaging device of claim 19, wherein the imaging probe is an ultrasound probe.

21. The imaging device of claim 19, further comprising:
memory coupled to the optical head assembly, the memory configured to store at least one of calibration information or usage information.

22. The imaging device of claim 19, wherein the optical head assembly wraps around the handle of the imaging probe and the handle of the imaging probe is configured to accept a physical coupling with the optical head assembly.

* * * * *